(12) United States Patent
Elbein et al.

(10) Patent No.: US 7,060,796 B2
(45) Date of Patent: Jun. 13, 2006

(54) ANTIBODY DIRECTED AGAINST PURIFIED β 1,2-XYLOSYLTRANSFERASE

(75) Inventors: Alan D. Elbein, Little Rock, AR (US); Gary A. Bannon, Little Rock, AR (US)

(73) Assignee: The Board of Trustees of the University of Arkanas, Little Rock, AR (US)

(*) Notice: Subject to any disclaimer, the term of this patent is extended or adjusted under 35 U.S.C. 154(b) by 61 days.

(21) Appl. No.: 10/411,905

(22) Filed: Apr. 11, 2003

(65) Prior Publication Data

US 2003/0166012 A1 Sep. 4, 2003

Related U.S. Application Data

(62) Division of application No. 09/748,578, filed on Dec. 22, 2000, now Pat. No. 6,593,462, which is a division of application No. 09/207,223, filed on Dec. 8, 1998, now Pat. No. 6,168,937.

(60) Provisional application No. 60/070,418, filed on Jan. 5, 1998, now abandoned, provisional application No. 60/067,932, filed on Dec. 8, 1997, now abandoned.

(51) Int. Cl.
*C07K 16/40* (2006.01)

(52) U.S. Cl. .................. 530/350; 530/387.9; 530/388.2

(58) Field of Classification Search ............. 530/387.1, 530/350, 387.9, 388.2, 387
See application file for complete search history.

(56) References Cited

OTHER PUBLICATIONS

A_Geneseq AAE10570, Oct. 2001.*
Zheng et al. J. Biol. Chem. 272(50) Dec. 12, 1997, pp. 31340-31347.*
Campbell, A.M. Monoclonal Antibody Technology, Elsevier Science Publishers BV, 1984, pp. 1-32.*
Moy et al. May 1996. The Journal of Cell Biology. vol. 133, No. 4, pp. 809-817.*

* cited by examiner

*Primary Examiner*—Christina Y. Chan
*Assistant Examiner*—Marianne DiBrino
(74) *Attorney, Agent, or Firm*—Benjamin Aaron Adler

(57) ABSTRACT

The present invention provides a purified, homogeneous plant enzyme that adds a β-1,2-linked xylose to the β-linked mannose on the N-linked oligosaccharides of storage glycoproteins. This β1,2-xylosyltransferase was purified from the microsomal fraction of soybean cells approximately 51,000-fold. Also provided is an antibody recognizing this β1,2-xylosyltransferase.

4 Claims, 13 Drawing Sheets

1 2 3 4 5 6 7 8 9 10 11 12 13 14

1 2 3 4 5 6 7 8 9 10 11 12 13

Peptide 1: 56 kDA band

Amino Acids: LSNEQEVFDSLK (SEQ ID NO. 1)

Peptide 2: 56 kDA band

Amino Acids: VLVDQEFLDEYVPR (SEQ ID NO. 2)

Peptide 3: 56 kDA band

Amino Acids: SQVQAIHDASVIIGAHGAGLTHIVSAL (SEQ ID NO. 3)

Peptide 1: 59 kDA band

Amino Acids: ELLVDQEFLDEYVPR (SEQ ID NO. 4)

Peptide 2: 59 kDA band

Amino Acids: GLEYHAINLG (SEQ ID NO. 5)

Fig. 4

```
                                                                                                                *
Xyl cln    AGGTTCTGGTTGACCAAGAGTTT TGGATGAGTATGTGCCAAGGGGAGGATTGATAGACACACCATGCGGGATTGATCGCC
Xyl pcr                            GAGTTTCTGATGAGTATGTGCCAAGGGGAGGATTGATAGACACACCATGCGGGATTGATCGCC
                                                                                      *  *
Xyl cln    AAGATTCGGATCGTGAGAGGGAAGGATTTCAATGTGATGAGTGGATTGAGGAACCAACACTTCTGGTGACACGTTTGAGTA
Xyl pcr    AAGATTCGGATCGTGAGAGGGAAGGATTTCAATGTGATGAGTGGATTGAGGAACCAACACTTCTGGTGACACGCTCTGAGTA Xyl cln    TGCTAAATCTTTTCACACTGTTACAGACTGGTACAGTGCTTATGTTTCTTCTAGAGTCACCGCTCTGCCTAATCGACCTCATG
Xyl pcr    TGCTAAATCTTTTCACACTGTTACAGACTGGTACAGTGCTTATGTTTCTTCTAGAGTCACCGCTCTGCCTAATCGACCTCATG
                                                                           *
Xyl cln    TGATCTTTGTTGATGGCCACTGTAAGGCTCCCTGAAGAGACATGGAAAAGCCTTATTCTCAAGCGTCGGATATGCTAAGAGC
Xyl pcr    TGATCTTTGTTGATGGCCACTGTAAGGCTCCCTGAAGAGACATGGAAAAGCCTTATTCTCAAGCGTCAGATATGCTAAGAGC Xyl cln    TTCAGTGGTTCAGTTTGTTTGTTTTCATCATGCTATTCTCTCACCCT-GGGATATGAGACGGCGGCAATGTTTAGAGGGCTTTCAGAACA
Xyl pcr    TTCAGTGGTTCAGTTTGTTTGTTTTCATCATGCTATTCTCTCACCCT-GGGATATGAGACGGCGGCAATGTTTAGAGGGCTTTCAGAACA Xyl cln    TATAGATTGTTATGGAGCAGCTCCTGCACAAGAACTATTGCAAAACCTTAATGACCACACAAAACCGCGCGCCTTTCTGAGTTTGGAG
Xyl pcr    TATAGATTGTTATGGAGCAGCTCCTGCACAAGAACTATTGCAAAACCTTAATGACCACACAAAACCGCGCGCCTTTCTGAGTTTGGAG Xyl cln    AAATGGTCAGAGCAGCTTTTGGGCTACCTTTAAATGTAAACCATGGAAAACCTCGCTGGACATAATGTCCTCTTTGTT
Xyl pcr    AAATGGTCAGAGCAGCTTTTGGGCTACCTTTAAATGTAAACCATGGAAAACCTCGCTGGACATAATGTCCTCTTTGTT Xyl cln    CGTCGCGAAGATTATTAGCTCATCCACGTCACAGTGGGAAACTTGAATCACGACTAAGTAACGAGCAAGAAGTCTTCAACTC
Xyl pcr    CGTCGCGAAGATTATTAGCTCATCCACGTCACAGTGGGAAACTTGAATCACGACTAAGTAACGAGCAAGAAGTCTTCAACTC Xyl cln    GTTGAAGAGCTGGGCATCCAATTATAAAGGGTGTAAAATTAACCTTGTCAACGGATTGTTTGCTCACATGTCTATGAAGGATC
Xyl pcr    GTTGAAGAGCTGGGCATCCAATTATAAAGGGTGTAAAATTAACCTTGTCAACGGATTGTTTGCTCACATGTCTATGAAGGATC
                                                *  *
Xyl cln    AGGTTCAAGCCATTCATGATGCATCGTCATCATTGGCGCCCATGGTGCCGGTC    (SEQ ID No. 6)
Xyl pcr    AGGTTCAAGCCATTCATGATGCATCGTCATCATAATCGGCGCCCATGGAG----   (SEQ ID No. 7)

Fig. 10
```

ANTIBODY DIRECTED AGAINST PURIFIED β 1,2-XYLOSYLTRANSFERASE

CROSS-REFERENCE TO RELATED APPLICATION

This patent application is a divisional of U.S. Ser. No. 09/748,578, filed on Dec. 22, 2000, now issued as U.S. Pat. No. 6,593,462 on Jul. 15, 2003, which is a divisional of U.S. Ser. No. 09/207,223, filed on Dec. 8, 1998, now issued as U.S. Pat. No. 6,168,937 on Jan. 2, 2001, which claims benefit of provisional patent application U.S. Ser. No. 60/070,418, filed Jan. 5, 1998, now abandoned, and provisional application U.S. Ser. No. 60/067,932, filed Dec. 8, 1997, now abandoned.

BACKGROUND OF THE INVENTION

1. Field of the Invention

The present invention relates generally to the fields of soybean enzymes and protein chemistry. More specifically, the present invention relates to purified β1,2-xylosyltransferase and uses thereof.

2. Description of the Related Art

Immediate hypersensitivity reactions to foods occurs in 6% to 8% of children, and about 1% of adults (1), and these reactions are mediated by the production of IgE antibodies to glycoproteins in these foods (2). The majority of allergies are to foods of plant origin, and a number of allergenic proteins have been identified from peanut, wheat, barley, rye and soy (3–7). While linear amino acid sequences and conformational structures of proteins have been identified as IgE-binding epitopes (8), there is increasing evidence (9–11) that specific carbohydrate structures may also be important as allergens.

While there is some similarity in peptide sequence between the different allergenic proteins, a common characteristic is that most contain N-linked oligosaccharides having a β1,2-linked xylose attached to the β-linked mannose of the core structure (12). Furthermore, in wheat and barley glycoproteins, xylose appears to be important for allergenicity, since those proteins containing a β1,2-xylose were more reactive in vivo and in vitro than deglycosylated proteins (13). In addition, IgE from allergic patients recognized an Endo-lys C peptide containing the glycan, and this recognition was lost upon deglycosylation (14).

The enzyme that adds xylose to these N-linked glycoproteins is the plant β1,2-xylosyltransferase. The identification of this enzyme in microsomes from *Phaseolus vulgaris* cotyledons (15), and from sycamore cells of *Acer pseudoplatanus* (16) has been reported, but there are no reports on the purification or properties of the enzyme. The substrate specificity for acceptor oligosaccharide was examined with particulate enzyme preparations from these two plant sources and in both cases, the enzymes acted on acceptors having a β1,2-GlcNAc residue on the Manα1,3-arm, but GlcNAc-Man$_5$(GlcNAc)$_2$ was not a good acceptor. Thus, in the processing pathway, xylose may be added after the mannosidase II step (15). However, with the xylosyltransferase from the snail, *Lymnaea stagnalis*, the biantennary oligosaccharide containing a galactose in β1,4 linkage to the GlcNAc on the Manα1,3-arm was also an acceptor, although it was much less efficient (17). These studies suggested that xylose is added after the removal of the two mannoses on the Manα1,6-arm, but before galactoses are added to the GlcNAc residues.

The xylose units on these N-linked oligosaccharides may play a critical role in allergenicity, and may also be important in regulating the structure of the oligosaccharide chains and the targeting of these proteins. Thus, it is important to purify this enzyme in order to study its properties and specificities in the absence of interfering activities and possible inhibitors.

The prior art is deficient in the lack of a purified β1,2-xylosyltransferase. The present invention fulfills this long-standing need and desire in the art.

SUMMARY OF THE INVENTION

In the present invention, the soybean xylosyltransferase was purified about 51,000-fold to near homogeneity, and the substrate specificities, and other properties of this enzyme were determined. Two protein bands labeled with the photoaffinity tag, azido-UDP[$^{32}$P]-xylose, were eluted from SDS gels, transferred to PVDF membranes, and digested with Endo lys C to obtain various peptides.

In one embodiment of the present invention, there is provided an isolated and purified plant enzyme that adds a β1,2-linked xylose to the F-linked mannose on the N-linked oligosaccharides of storage glycoproteins. Preferably, the enzyme is β1,2-xylosyltransferase. β1,2-xylosyltransferase releases peptides having the sequence selected from the group consisting of SEQ ID Nos. 1–5 upon digestion by Endo lys C. Preferably, the enzyme is obtained from the microsomal fraction of soybean cells and has a purity of about 51,000-fold to near homogeneity compared to a solubilized enzyme fraction. This β1,2-xylosyltransferase is separated on SDS gels into 56 and 59 kDa bands.

In another embodiment of the present invention, there is provided one or more oligonucleotides for cloning the gene encoding β1,2-xylosyltransferase, wherein the oligonucleotides are generated from the peptide having the sequence selected from the group consisting of SEQ ID Nos. 1–5.

In still another embodiment of the present invention, there is provided DNA encoding β1,2-xylosyltransferase selected from the group consisting of: (a) isolated DNA which encodes a xylosyltransferase; (b) isolated DNA which hybridizes to isolated DNA of (a) and which encodes a xylosyltransferase; and (c) isolated DNA differing from the isolated DNAs of (a) and (b) in codon sequence due to the degeneracy of the genetic code, and which encodes a xylosyltransferase. Preferably, the DNA has a sequence shown in SEQ ID No. 6.

In yet another embodiment of the present invention, there is provided an antibody directed against β1,2-xylosyltransferase. Preferably, this antibody can be used for localizing xylosyltransferase in a plant cell by contacting the cell with the antibody and then detecting localization of the antibody, wherein the localization of the antibody indicates the localization of the enzyme. Further, the antibody can be used for determining distribution levels of xylosyltransferase in a plant by contacting the plant with the antibody and then detecting binding activity of the antibody, wherein a higher activity indicates a higher level of xylosyltransferase in the test plant.

In still yet another embodiment of the present invention, there is provided a method for determining the effect of xylosylation of animal glycoproteins by transfecting the DNA encoding β1,2-xylosyltransferase into the animal cells.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 3 shows photolabeling studies of XT with $N_3$-UDP [$^{32}$P]-xylose.

FIG. 4 shows the amino acid sequences of several peptides released by Endo lys C digestion of purified xylosyltransferase and isolation and sequencing by Harvard Microchemical Systems. These sequences showed no homology to any known proteins by a BLAST search.

FIG. 6L (Oligosaccharide 12) has been characterized as the product resulting from enzymatic activity with acceptor oligosaccharide 4.

FIG. 10 shows a comparison of the nucleotide sequences from the XT PCR product (SEQ ID No. 7) and the XT cDNA clone (SEQ ID No. 6). Differences between the two sequences are noted by bold asterisks. The minor differences could be due to mistakes made by the Taq polymerase or they may represent the products of two separate but highly homologous genes. Only the region of the XT cDNA clone that overlaps with the PCR product is shown.

DETAILED DESCRIPTION OF THE INVENTION

Figure 1:
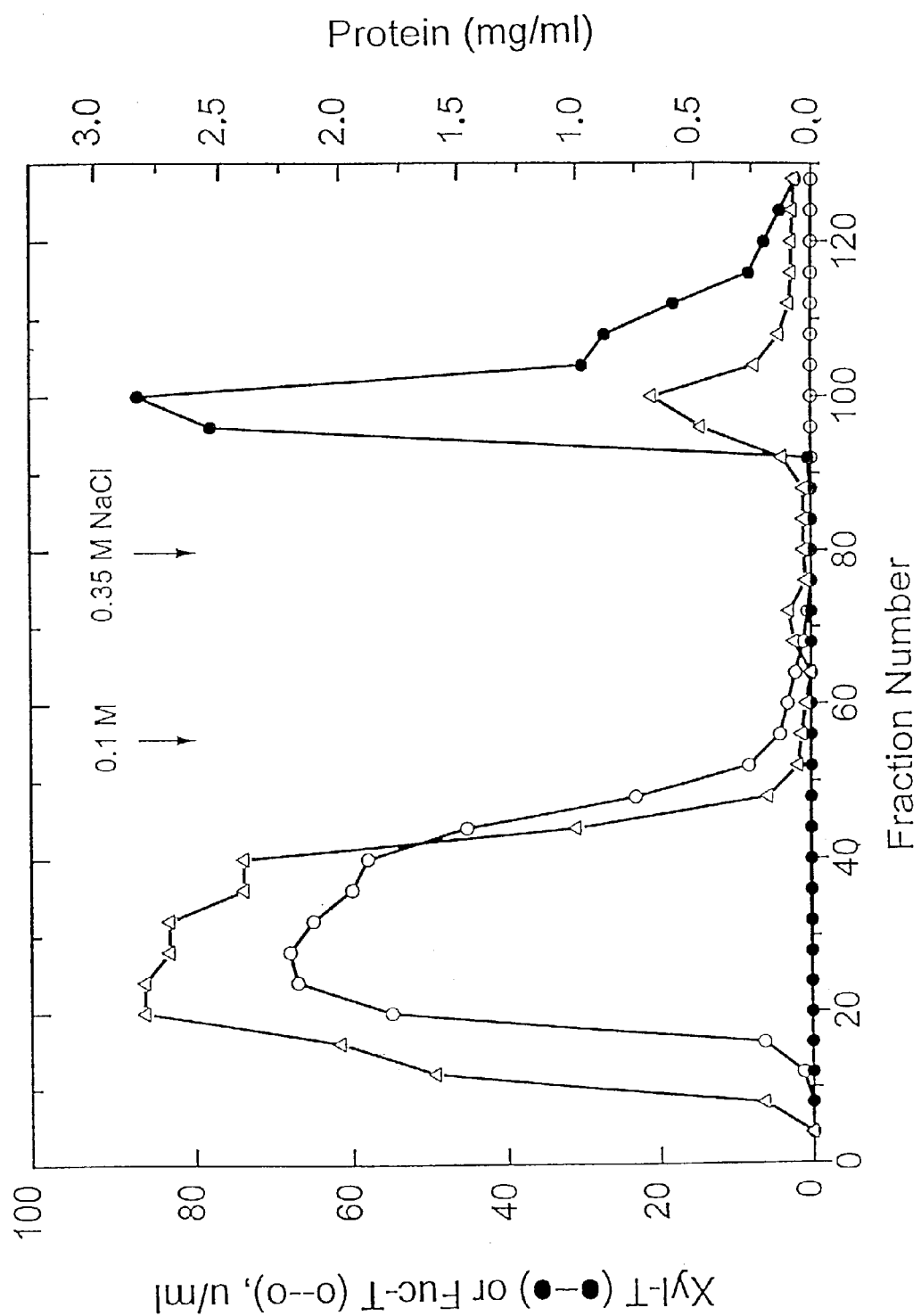
FIG. 1 shows the purification of the soybean xylosyltransferase on a column of cellulose-phosphate.

The enzyme that transfers xylose units from UDP-D-xylose to the β-linked mannose of the N-linked oligosaccharides was purified about 51,000-fold from the microsomal fraction of soybean cells. The enzyme was solubilized from the membranes with 1% Triton X-100, and purified by chromatography on cellulose phosphate, iminodiacetic acid-SEPHAROSE, yellow-3-agarose and UDP-hexanolamine-SEPHAROSE. At the highest stage of purity, 2 major protein bands of 56 and 59 kDa were detected, and both of these bands became specifically labeled when incubated with the photoaffinity tag 5-$N_3$-UDP[$^{32}$P]-xylose and exposed to UV light. Labeling of the proteins was specific since it was inhibited by adding increasing amounts of unlabeled UDP-xylose. The two protein bands were eluted from SDS gels, transferred to PVDF membranes, and subjected to limited proteolysis and amino acid sequencing of several isolated peptides. The peptide maps and amino acid sequences suggested that both proteins were closely related. These sequences did not show substantial homology to other known sequences in a BLAST search. The activity of the enzyme was assayed by following the transfer of $^3$H-xylose from UDP-[$^3$H]xylose to oligosaccharide acceptor by gel filtration or ion-exchange chromatography. Both assays showed good linearity with respect to both time of incubation and concentration of enzyme. The specificity of the enzyme for oligosaccharide acceptor indicated that the biantennary oligosaccharide, $(GlcNAc)_2Man_3GlcNAc$-GlcNAc, was the best acceptor, although the same oligosaccharide with an β1,6-linked L-fucose on the reducing GlcNAc was also a reasonably good acceptor. Oligosaccharides having one or two terminal galactoses at the reducing end, such as $Gal_2GlcNAc_2Man_3GlcNAc$-GlcNAc, were not acceptors of xylose, nor were oligosaccharides lacking terminal GlcNAc residues. The enzyme was also specific for UDP-xylose, and UDP-glucose was neither a glycosyl donor, nor an inhibitor of the transferase. The purified xylosyltransferase was only slightly stimulated by the addition of divalent cations, and was not inhibited by addition of, or dialysis against, EDTA. Some other properties of this enzyme are also presented. The purified enzyme was stable to storage at −20° C. for several months without loss of activity. The product of the reaction was shown by chromatography and by NMR spectroscopy to be the oligosaccharide acceptor with a β1,2-linked xylose on the α-linked mannose.

In one embodiment of the present invention, there is provided an isolated and purified plant enzyme that adds a β1,2-linked xylose to the β-linked mannose on the N-linked oligosaccharides of storage glycoproteins. Preferably, the enzyme is β1,2-xylosyltransferase. β1,2-xylosyltransferase releases peptides having the sequence selected from the group consisting of SEQ ID Nos. 1–5 upon digestion by Endo lys C. Preferably, the enzyme is obtained from the microsomal fraction of soybean cells and has a purity of about 51,000-fold to near homogeneity compared to a solubilized enzyme fraction. Further, β1,2-xylosyltransferase is separated on SDS gels into 56 and 59 kDa bands.

In another embodiment of the present invention, there are provided oligonucleotides for cloning the gene encoding β1,2-xylosyltransferase, wherein the oligonucleotides are generated from the peptide having the sequence selected from the group consisting o f SEQ ID Nos. 1–5.

In still another embodiment of the present invention, there is provided DNA encoding β1,2-xylosyltransferase selected from the group consisting of: (a) isolated DNA which encodes a xylosyltransferase; (b) isolated DNA which hybridizes to isolated DNA of (a) and which encodes a xylosyltransferase; and (c) isolated DNA differing from the isolated DNAs of (a) and (b) in codon sequence due to the degeneracy of the genetic code, and which encodes a xylosyltransferase. Preferably, the DNA has a sequence shown in SEQ ID No. 6.

In yet another embodiment of the present invention, there is provided an antibody directed against β1,2-xylosyltransferase. Preferably, this antibody can be used for localizing xylosyltransferase in a plant cell by contacting the cell with the antibody and then detecting localization of the antibody, wherein the localization of the antibody indicates the localization of the enzyme. Further, the antibody can be used for determining distribution levels of xylosyltransferase in a plant by contacting the plant with the antibody and then detecting binding activity of the antibody, wherein a higher activity indicates a higher level of xylosyltransferase in the test plant.

In still yet another embodiment of the present invention, there is provided a method for determining the effect of xylosylation of animal glycoproteins by transfecting the DNA encoding β1,2-xylosyltransferase into the animal cells.

The following examples are given for the purpose of illustrating various embodiments of the invention and are not meant to limit the present invention in any fashion.

EXAMPLE 1

Materials

UDP-[$^3$H]xylose (7.5 Ci/mmol) and GDP-L-[$^3$H]fucose (7.1 Ci/mmol) were purchased from American Radiolabeled Co. [2-$^3$H]mannose (15 Ci/mmol) and [6-$^3$H]galactose (20 Ci/mmol) were from New England Nuclear Co. Radioactive compounds were checked by chromatography before use. Various adsorbents were obtained from the following sources: DEAE-cellulose (DE-52) from Whatman Co. and UDP-hexanolamine-SEPHARSE, SEPHACRYL S-300, red-SEPHAROSE, phenyl-SEPHAROSE and DEAE-Cibracon Blue 3GA from Sigma Chemical Co. The following materials were obtained from Biorad Co: SDS, acrylamide, bisacrylamide, Coomassie Blue, protein assay reagent, hydroxylapatite, and AFFI-GEL 501. All other chemicals were from reliable chemical sources, and were of the best grade available.

EXAMPLE 2

Assay for Xylosyltransferase Activity

Reaction mixtures for the assay of β1,2-xylosyltransferase contained the following components in a final volume of 25 μl: 100 mM MES buffer, pH 7.0, 10 mM $MnCl_2$, 0.2% Triton X-100, 5 mM ATP, 0.2 mM UDP-[$^3$H]xylose (15,000 cpm), and 4 nmol of oligosaccharide acceptor (usually $GlcNAc_2$-$Man_3$-$GlcNAc_2$-tyrosinamide (FIG. 6D); or the asialo-agalacto-oligosaccharide from transferrin). The reaction was started by the addition of 5 μl of the enzyme solution, and incubations were usually at 37° C. for 1 hour. The reaction was stopped by the addition of 100 μl of 1% acetic acid, and the reaction mixtures were chromatographed on a column of Biogel P-4 prepared by placing 8 ml of gel into a 10 ml pipette. The columns were equilibrated with 1% acetic acid, and the product was separated from substrates by elution with 1% acetic acid containing 0.2 M NaCl. The xylosylated oligosaccharide product emerged within 2.5 to 7 ml of elution, whereas the UDP-xylose substrate eluted after 10 ml of elution fluid.

When more purified enzyme preparations were used in the assays, the radiolabeled product could be separated from the radioactive substrate by ion-exchange chromatography on an Amberlite column (or a column of DOWEX-1-Cl$^-$) contained in a Pasteur pipette. In this case, the substrate, UDP-xylose, binds to the column whereas the product ($^3$H-xylose-oligosaccharide) emerges in the wash. Thus the wash can be counted as a measure of radioactive xylose transferred to oligosaccharide. In these assays, it is important to be certain that the enzyme preparation is free of degradative enzymes that cleave UDP-xylose to free xylose.

EXAMPLE 3

Preparation of Oligosaccharide Substrates for the Enzyme

Asialo-agalacto-oligosaccharide was prepared from transferrin by the following procedure. Transferrin was obtained from Sigma Chemical Co. and was exhaustively digested with pronase. Thus, 500 mg of transferrin was dissolved in 25 ml of 50 mM Tris-HCl buffer, pH 7.5 containing 2 mM $CaCl_2$, and 2 mg/ml of pronase were added. The incubations were allowed to proceed for 24 hours under a toluene atmosphere and another 2 mg/ml of pronase were added for an additional 24 hours. At the end of this time, 25 ml of 10% trichloroacetic acid (TCA) were added and the mixture was stirred vigorously and cooled on ice for 30 min. The precipitate was removed by centrifugation and the TCA was extracted from the supernatant liquid by repeated addition and removal of ethyl ether until the solution was close to neutrality. The aqueous phase was concentrated to a small volume, and the glycopeptide was purified on a 2×200 cm column of Biogel P-4. The glycopeptide was then heated at 80° for 4 hours in 4 M acetic acid to release the sialic acid and the asialo-glycopeptide was again purified on the Biogel P-4 column. The asialo-glycopeptide was then incubated with several batches of bovine liver β-galactosidase to remove the terminal galactose residues. This final product was purified on the Biogel P-4 column, and its concentration was determined by the anthrone method, using mannose as a standard.

Figure 6A:
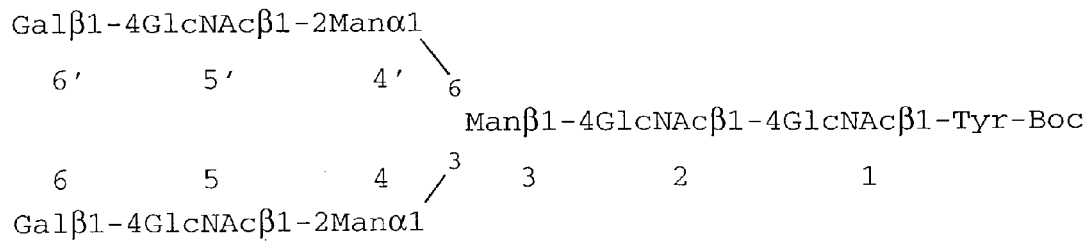
FIGS. 6A–6L show the structures of tyrosinamide oligosaccharide. The structures of FIGS. 6A–6K (oligosaccharides 1 through 11), discussed in the text are shown. Each oligosaccharide contains a β-glycosylamide linkaged to Box-tyrosine.
Figure 6B:
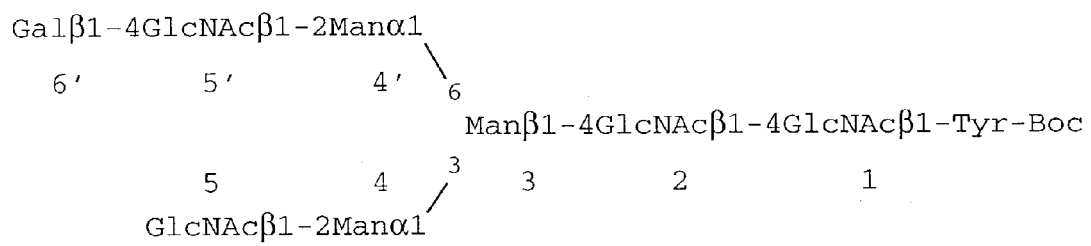
Figure 6C:
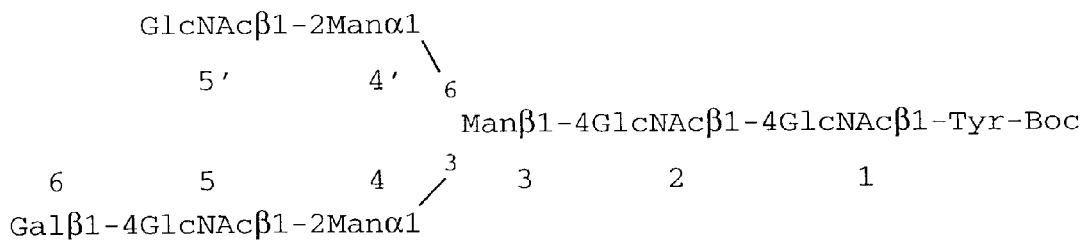

Tyrosinamide biantennary oligosaccharides, with or without a core fucose (see FIGS. 6A–6L for structures), were prepared from bovine fetuin and porcine fibrinogen as described (18,19). A biantennary oligosaccharide (FIG. 6A) was converted into various xylosyltransferase acceptor substrates as follows: Oligosaccharide 1 (1 μmol) was treated with 16.5 mU of bovine testis β-galactosidase (EC 3.2.1.23 from Boehringer Mannheim) in 100 μl of 100 mM phosphate-citrate buffer, pH 4.3 at 37° C. for 4 hours. The reaction was stopped by boiling for 5 minutes. The partially degalactosylated biantennary structure was reacted with 500 mU (2 ul) of hexosaminidase (EC 3.2.1.52 from V-labs), for 12 hours at 37°. The 4 product peaks were purified on a semi-preparative RP-HPLC C-18 column run at 50° and the column was eluted at 3 ml/min with 14% acetonitrile in 0.1% acetic acid. Peaks were detected by monitoring at 280 nm. The second and third peak were treated individually with 3 mU β-galactosidase in 10 μl of 100 mM phosphate-citrate buffer, pH 4.3, for 24 hours at 37°. The final products were purified on a polymeric PRP-1 RP-HPLC column which was eluted with 13% acetonitrile in 0.1% acetic acid at 2 ml/min. Peaks were detected at 280 nm and fractions were collected and freeze dried. The overall yield was about 30%. The identity of each oligosaccharide product was established by NMR and ES-MS as described (18,19).

EXAMPLE 4

Preparation of Azido-Labeled UDP[$^{32}$P]-xylose Substrate Analog

Azido-UDP[$^{32}$P]-xylose was prepared from azido-UDP [$^{32}$P]-glucuronic acid using the purified UDP-glucuronic acid carboxylyase as described (21). This procedure involved the synthesis of azido-UDP[$^{32}$P]-glucose from glucose-1[$^{32}$P] and UTP by published methods (22), conversion of this $N_3$-UDP[$^{32}$P]-glucose to $N_3$-UDP[$^{32}$P]-glucuronic acid by the UDP-glucose dehydrogenase, and then decarboxylation of the $N_3$-UDP[$^{32}$P]-glucuronic acid to $N_3$-UDP[$^{32}$P]-xylose using the partially purified UDP-glucuronic acid carboxylyase from wheat germ (21).

For the synthesis of 5-azido-UDP[$^{32}$P]-xylose, 1 ml of 20 μM 5-azido-UDP[$^{32}$P]-glucuronic acid in methanol was placed in a tube and the solvent was removed under a stream of nitrogen. To this sample, 1 mg of hydroxylapatite-purified carboxylyase was added along with 300 μl of 0.1 M sodium phosphate buffer, pH 7.0, containing 0.5 g/l of EDTA and 0.5 ml/l of 2-mercaptoethanol. The mixture was incubated for 3 hours at 37°, at which time the reaction mixture was loaded onto a column (1×5 cm) of DEAE cellulose. The resin was washed thoroughly with water, and the nucleoside diphosphate sugars were eluted with a linear gradient [300 ml of 0 to 0.4 M] of sodium bicarbonate. With this gradient, UDP-xylose emerges from the column first and was well separated from UDP-glucuronic acid. The product was further characterized by its UV spectrum, its mobility on paper and thin layer chromatograms, and by identification of the products released by treatment with alkaline phosphatase and snake venom phosphodiesterase.

EXAMPLE 5

Preparation of Microsomes from Soybean Cells

Soybean cells were routinely grown for 7 days at 28° C. in suspension culture in 500 ml erlenmeyer flasks containing 100 ml of B-5 medium (23). This medium has the following composition (mg/ml) $KNO_3$, 3000; $(NH_4)_2SO_4$, 134; $MgSO_4.7H_2O$, 500; $CaCl_2.7H_2O$, 150; $NaH_2PO_4.H_2O$, 150; $MnSO_4.H_2O$, 100; KI, 0.75; $H_3BO_3$, 3; $ZnSO_4.7 H_2O$, 2; $CuSO_4$, 0.025; $Na_2MoO_4.2H_2O$, 0.25; $CoCl_2.6H_2O$, 0.025; EDTA-ferric sodium salt, 28; myoinositol, 100; thiamin-.HCl, 10; nicotinic acid, 1; pyridoxine.HCl, 1; sucrose, 20,000; 2,4-dichlorophenoxyacetic acid, 0.5. The final solution was adjusted to pH 5.5. Cells were harvested by filtration at the mid-log phase of growth and washed well with water and then with Buffer A (25 mM HEPES, pH 7.2, containing 0.25 M sucrose, 0.5 M DTT, 1 mM EDTA and 0.5 mM PMSF). About 100 g of washed cells were suspended in 300 ml of Buffer A and disrupted by sonic oscillation (three 5 minute periods of sonication at 80% output, with 10 min of cooling on ice between each sonication). The suspension was centrifuged at 3000 g for 15 minutes to remove unbroken cells, nuclei and mitochondria, and the supernatant liquid was then centrifuged at 100,000 g to isolate the microsomal fraction. The microsomal pellet was resuspended in Buffer B (25 mM HEPES, pH 7.2, containing 10% glycerol, 0.1 M NaCl, 1 mM DTT, 1 mM EDTA and 1 mM PMSF).

EXAMPLE 6

Purification of the Xylosyltransaferase

The microsomal fraction from soybean cells transferred xylose from UDP-xylose to $GlcNAc_2Man_3(GlcNAc)_2$-tyrosinamide (or peptide). In order to purify this glycosyltransferase, it was necessary to solubilize the enzyme from the microsomes. A variety of detergents were tested at different concentrations for their ability to solubilize the xylosyltransferase and maintain its stability. Table 1 shows that in each case, the enzyme was mixed with detergent, and the mixture was stirred on ice for 15 minutes and then centrifuged at high speed for 30 minutes to pellet the membranes. The enzymatic activity in the supernatant liquid was then measured in the usual transferase assay. As seen in Table 1, the activity was best solubilized from the membranes by treatment with either 1% or 2% Triton X-100 in Buffer B. Thus, at either concentration of Triton X-100, at least 80% of the enzymatic activity was recovered in the supernatant liquid, and the enzyme appeared to be fairly stable under these conditions.

TABLE 1

Solubilization of Xylosyltransferase by Detergents

| Detergent | Xylose Transferred to Acceptor (cpm)* | |
|---|---|---|
| | Particulate Suspension* | High Speed Supernatant |
| None | 1971 | 325 |
| Triton x-100, 0.5% | 2481 | 1189 |
| Triton x-100, 1% | 2689 | 2188 |
| Triton x-100, 2% | 2695 | 2297 |
| Taurocholoate, 1% | 1570 | 1574 |
| Deoxycholate, 1% | 316 | 197 |
| CPC, 1% | 1341 | 64 |
| Octylglucoside, 1% | 2395 | 210 |
| CHAPS, 1% | 2168 | 541 |
| SDS, 1% | 144 | 27 |

*the amount of protein was adjusted to a common value (10 mg/ml), so that each enzyme solution could be directly compared.

As a result of these experiments, large scale preparations of solubilized enzyme were made using 1% Triton X-100, with stirring for 30 minutes. The mixture was then centrifuged at 100,000 g for 1 hour, and the pellet was resuspended in Buffer B containing 1% Triton X-100 and centrifuged again at 100,000 g for 30 minutes. The two supernatant fractions were pooled for further purification steps. Eighty to ninety percent of the xylosyltransferase activity was recovered in the pooled supernatant fraction after this treatment, whereas in control membranes that were stirred on ice for 30 minutes in buffer but without detergent, more than 85% of the activity was pelleted when centrifuged at 100,000 g for 1 hour. In many cases, the supernatant liquids were used immediately in further purification steps, but they could be stored at –800° for a month with little loss of xylosyltransferase activity.

The solubilized enzyme was then purified on a 2×20 cm column of cellulose phosphate that had been equilibrated with Buffer C (25 mM Hepes buffer, pH 7.2, containing 10% glycerol, 0.15% Triton X-100, and 0.5 mM dithiothreitol). After applying the enzyme solution, the column was washed with Buffer C, followed by Buffer C containing 100 mM NaCl, until no more protein was eluted. As shown in FIG. 1, the enzyme was eluted from the column with Buffer C, containing 500 mM NaCl. Fractions were assayed for xylosyltransferase activity and active fractions were pooled, concentrated to a small volume, and dialyzed against Buffer C. This step gave an approximately ten-fold increase in specific activity with an 87% recovery of activity (Table 2).

TABLE 2

Summary of the Soybean Cell Xylosyltransferase Purification

| Step | Total Protein (mg) | Total Units* (U-units) | Specific Activity (U/mg) | Purification Factor (Fold) | Recovery (%) |
|---|---|---|---|---|---|
| Microsomal Fraction | 2894 | 25127 | 8.7 | 1 | 100 |
| Phospho-cellulose | 84.2 | 26306 | 193 | 22 | 64.9 |
| IDA-Sepharose | 6.5 | 13272 | 2041 | 234 | 52.8 |
| Yellow 3-Agarose | 2.1 | 8105 | 3859 | 443 | 32.2 |
| UDP-hexanolamine | 0.006** | 2672 | 445333 | 51187 | 10.6 |

*A unit is defined as the amount of enzyme which transfers 1 nmole of xylose to acceptor per hour.
**This amount of protein was estimated by comparing the staining of the xylosyltransferase on SDS gels to staining of known amounts of bovine scrum albumin.

Figure 2:
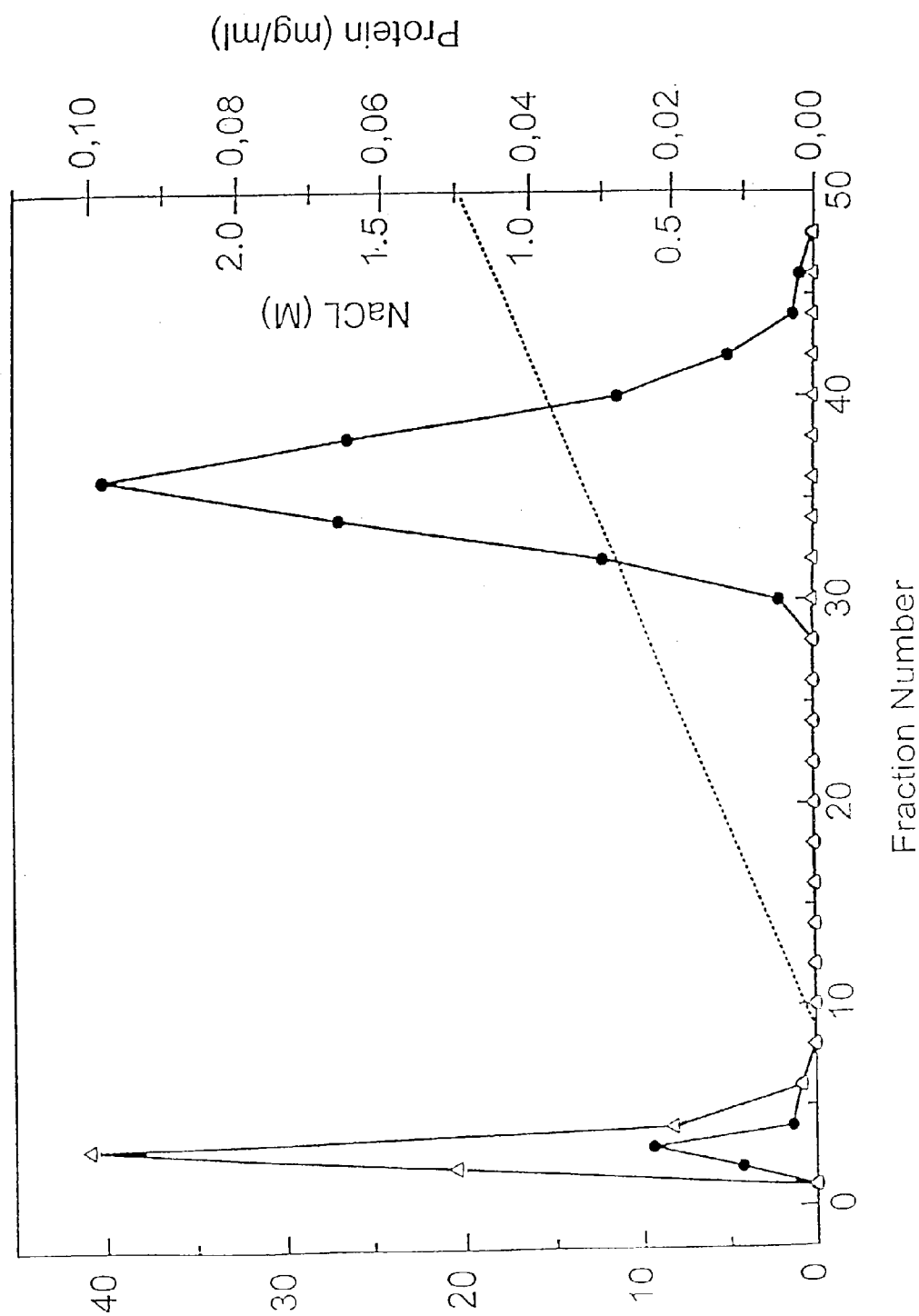
FIG. 2 shows the purification of the xylosyltransferase (XT) on a column of UDP-hexanolamine-sepharose.

The dialyzed enzyme fraction was applied to a 1×10 cm column of UDP-hexanolamine-Sepharose that had been equilibrated with Buffer C. The column was first washed with 100 ml of Buffer C and then with 100 ml of Buffer C, containing 15% glycerol and 0.3 M NaCl, followed by Buffer C, glycerol and 1 M NaCl. As shown in FIG. 2, the xylosyltransferase was eluted at 1 M NaCl. Fractions containing transferase activity were pooled, concentrated, and dialyzed against Buffer C containing 15% glycerol. This affinity step increased the specific activity by a factor of about 280-fold with a total recovery of about 55%.

Using these purification steps, the xylosyltransferase was purified about 51,000-fold from the solubilized enzyme fraction. The summary of the purification procedure is presented in Table 2 and shows that the overall recovery of activity was about 10%. FIG. 3 demonstrates that at the final step of purification, two major protein bands of 56 and 59 kDa were detected. In order to determine which band was really the xylosyltransferase, the enzyme fraction from UDP-hexanolamine-Sepharose was incubated with azido-UDP[$^{32}$P]-xylose, and after 30 sec., the mixture was exposed to UV light to activate the azido group. The proteins in the incubation mixture were then separated by SDS-PAGE, and the gels were exposed to film to locate the labeled protein(s).

Figure 3A:
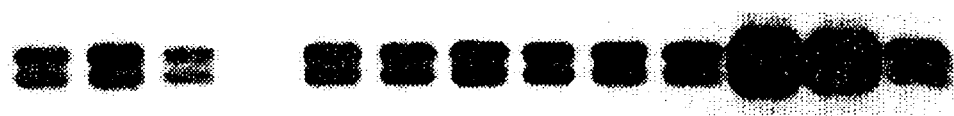
In FIG. 3A, lanes are: 1–3, 1, 2.5 and 5 µl UDP-xylose probe; all other lanes have 5 µl of probe plus: lanes 4 and 5, 10 and 100 µM unlabeled UDP-xylose; 6 and 7, 10 and 100 µM UDP-galactose; 8 and 9, 10 and 100 µM UDP-glucose; 10 and 11, 10 and 100 µM UDP-glucuronic acid; 12, oligosaccharide 4; 13, oligosaccharide 9; 14, oligosaccharide 8.

Lanes 1–3 of FIG. 3A, shows that both the 56 and the 59 kDa protein became labeled with the UDP-xylose probe when exposed to UV, and this labeling increased with increasing concentrations of the probe. As expected, when the incubation mixture was not exposed to UV light, no labeled proteins were detected on the gels (data not shown). Lanes 4 and 5 show that when the photolabeling was done in the presence of increasing amounts of unlabeled UDP-xylose (0.1, 1 and 10 μM UDP-xylose), the amount of radioactivity associated with the 56 and 59 kDa bands was greatly diminished indicating that labeling by this probe is specific for the xylosyltransferase. Incubation of enzyme and probe in the presence of other nucleoside diphosphate sugars such as UDP-glucose (10 and 100 μM, lanes 6 and 7), UDP-galactose (10 and 100 μM, lanes 8 and 9) or UDP-glucuronic acid (10 and 100 uM, lanes 10 and 11) did not inhibit the amount of radiolabel in the xylosyltransferase. Interestingly enough, addition of oligosaccharides that are good acceptors of xylose (FIG. 6D or 6J) greatly stimulated binding of UDP-xylose (lanes 12 and 13) whereas oligosaccharides that are not good acceptors (lane 14) did not stimulate UDP-xylose binding.

Figure 3B:
In FIG. 3B, effects of various amounts of acceptor oligosaccharides on labeling with UDP-xylose probe are shown. All lanes have 5 µl of $N_3$-UDP[$^{32}$P]-xylose plus: lane 1, no acceptor; lanes 2–5, 4, 10, 30, 80 µM oligosaccharide 4; lanes 6–9, 4, 10, 30, 80 µM oligo 9; lanes 10–13, 80 µM inactive oligosaccharides.

FIG. 3B shows concentration effects of oligosaccharide acceptors in terms of their stimulation of UDP-xylose binding. Thus, lane 1 is without oligosaccharide acceptor while lanes 2–5 are with 4, 10, 30 and 80 μM oligosaccharide 4 and lanes 6–9 with oligoscacharide 10. Lanes 10–13 are with various oligosaccharides that are inactive as acceptors (i.e., 1, 5, 6, 7).

EXAMPLE 7

Amino Acid Sequence of the Purified Xylosyltransferase

Since the evidence indicated that both the 56 kDa protein and the 59 kDa protein recognized UDP-xylose as a substrate, and both were present in the most purified enzyme preparation, sufficient amounts of both proteins were isolated, transferred to PVDF membranes and sent to Harvard Microchemistry Laboratories for isolation of peptides and amino acid sequencing. The peptide maps of these two proteins, obtained by Endo Lys C digestion and HPLC, were very similar in structure, but indicated enough differences to show that they were not related by a proteolytic removal of a 3 kDa peptide. The sequence data for several peptides derived from each of these two proteins is shown in FIG. 4. Comparison of the peptide sequences with known protein sequences by a BLAST search indicates that these proteins share very little homology with reported proteins.

EXAMPLE 8

Stability of the Purified Enzyme

Figure 5:
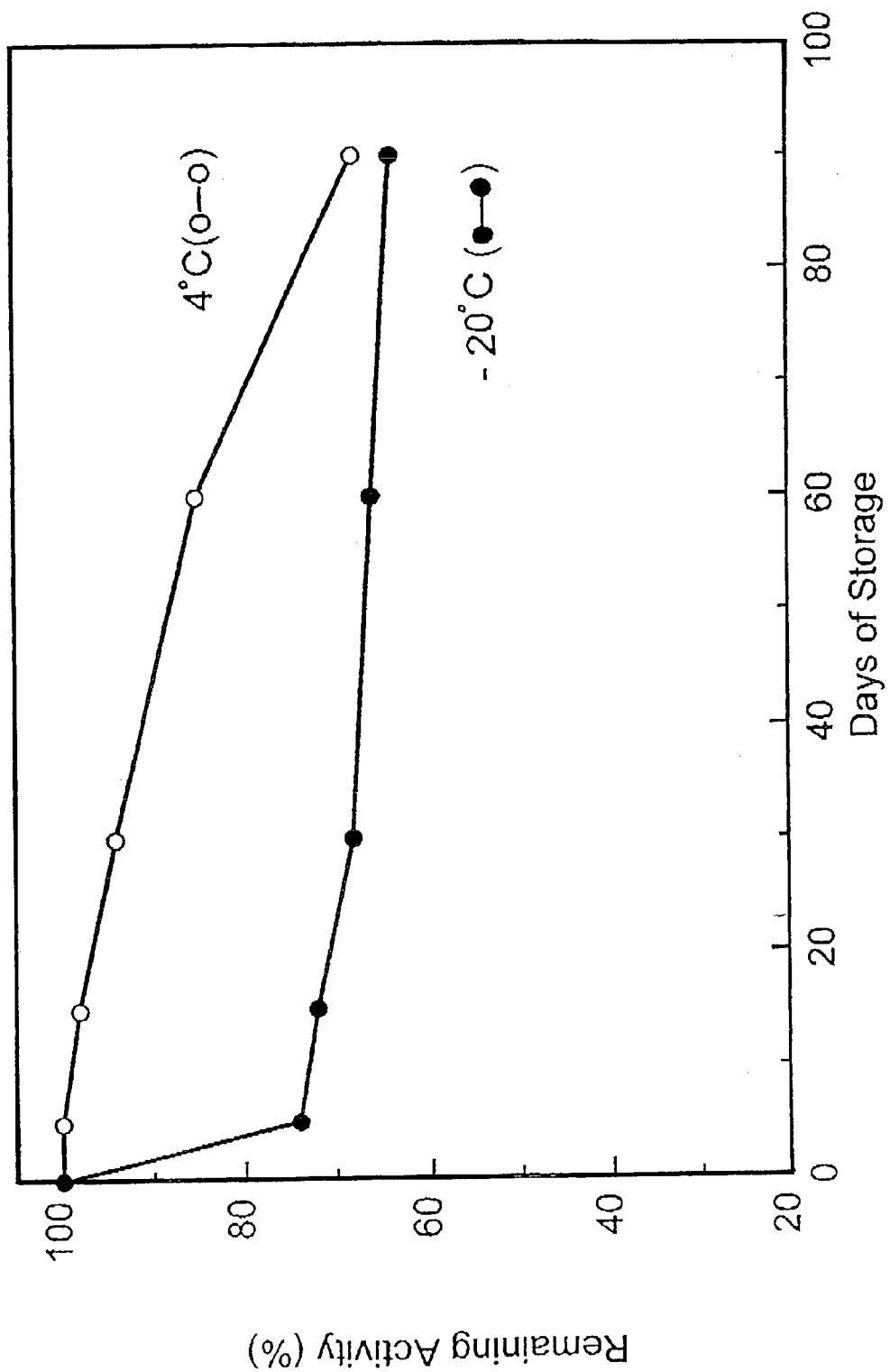
FIG. 5 shows the stability of the purified xylosyltransferase to storage in an ice bucket (4° C.) or at −20° C. Enzyme from cellulose-phosphate or from UDP-hexanolamine was stored in 1 ml aliquots in 25 mM HEPES buffer, pH 7.0, containing 10% glycerol, 0.2% Triton X-100 and 1 mM dithiothreitol. At various times shown in the Figure, an aliquot of the enzyme was removed and thawed (if necessary) and assayed for enzymatic activity in the usual assay.

The xylosyltransferase, eluted from the UDP-hexanolamine-Sepharose column, was examined for its stability under various conditions. FIG. 5 shows that the enzyme was reasonably stable for up to 90 days, when dissolved in 25 mM Hepes buffer, pH 7.0, containing 10% glycerol, 0.2% Triton X-100 and 1 mM DTT, and kept either in an ice bucket at 4°, or at –20°. After a month of storage under these conditions and at either temperature, at least 80% of the original enzyme activity still remained. These data indicate that storage of the purified enzyme in the above buffer solution is not a problem. The stability of the enzyme is, however, sensitive to changes in the pH of the storage solution. Thus, above pH 7.5 and below pH 6.5, the stability of the enzyme rapidly declines at either temperature.

EXAMPLE 9

Synthesis of Oligosaccharide Acceptor Substrates

Exoglycosidase trimming was used to convert biantennary substrates (see FIGS. 6A–6L) for structures of oligosaccharides) into substructures that could serve as xylosyl acceptors. Treatment of substrate 1 with β-galactosidase resulted in its complete conversion into substrate 4, and subsequent treatment with β-hexosaminidase resulted in the formation of oligosaccharide 7. Likewise, β-galactosidase and β-hexosaminidase digestions were used to prepare oligosaccharides 10 and 11, starting with a core fucosylated biantennary oligosaccharide obtained from porcine fibrinogen.

Figure 6D:
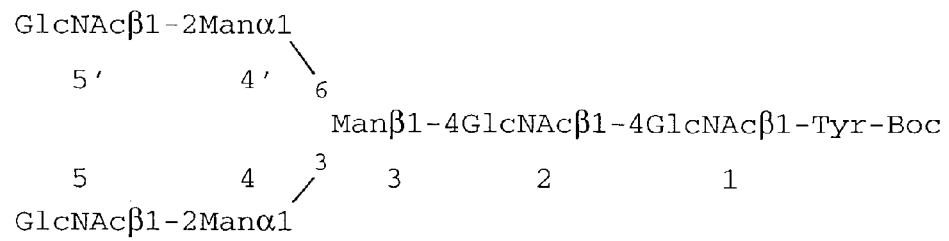
Figure 6E:
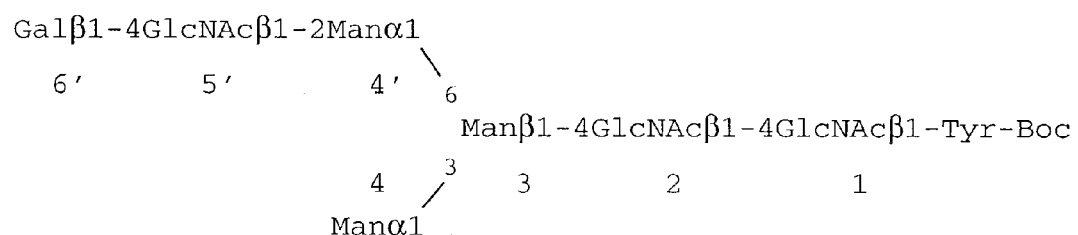
Figure 6F:
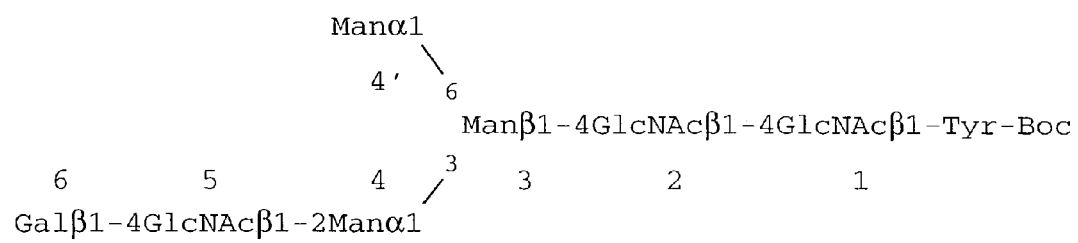
Figure 6G:
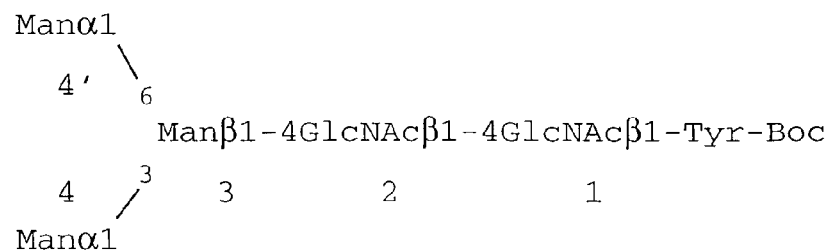
Figure 6H:
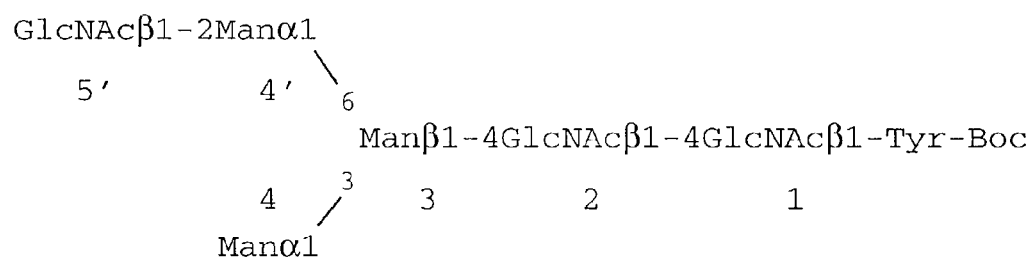
Figure 6I:
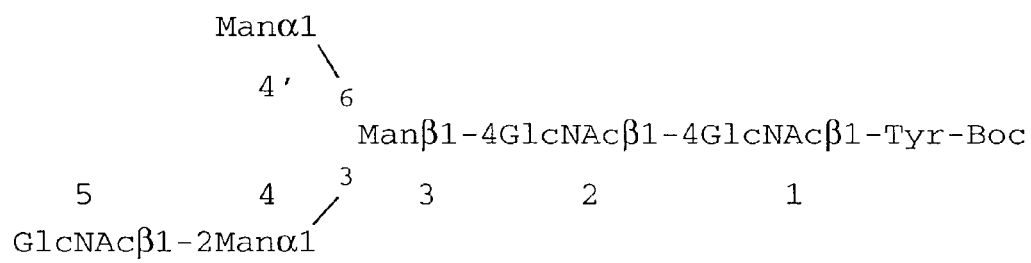
Figure 6J:
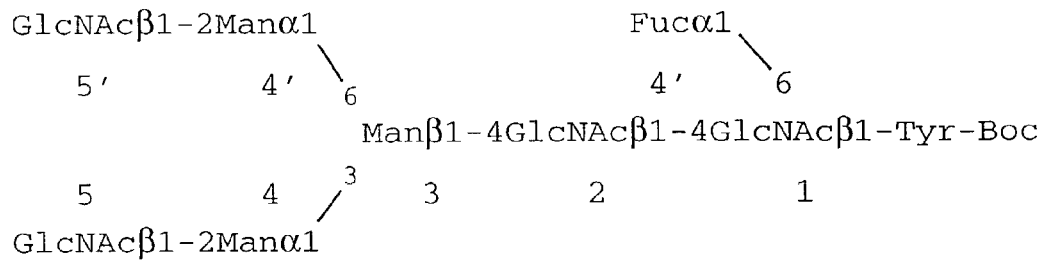
Figure 6K:
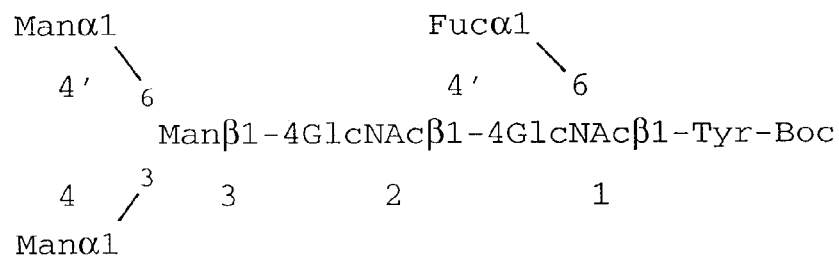
Figure 6L:
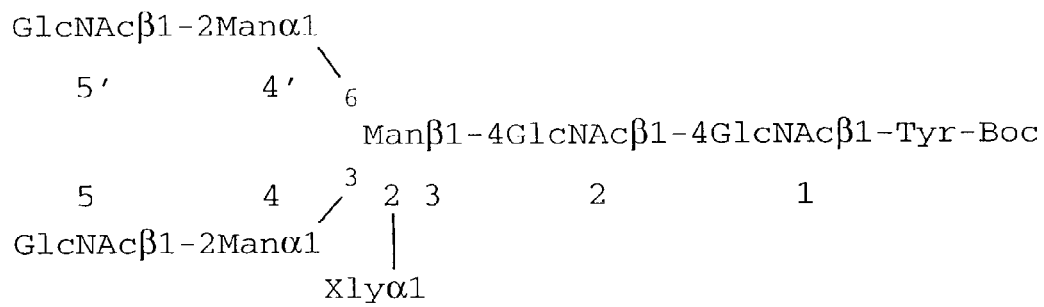
Figure 7:
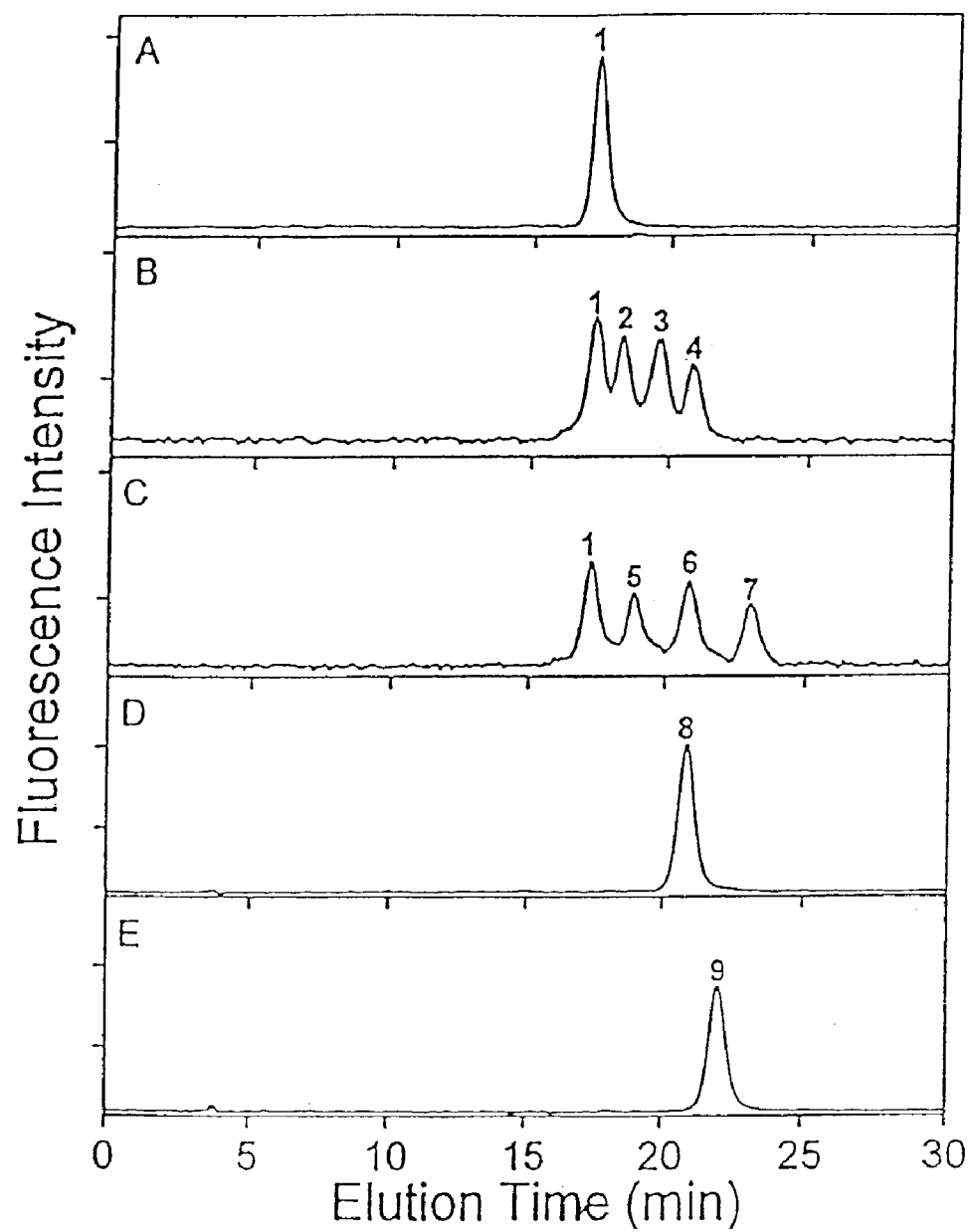
FIG. 7 shows the RP-HPLC analysis of oligosaccharide trimming reactions: Asymmetric trimming of tyrosinamide biantennary oligosaccharide was monitored by RP-HPLC using fluorescence detection. Partial removal of galactose from oligosaccharide 1 (panel A) resulted in the formation of peaks 2, 3 and 4, as shown in panel B. Subsequent treatment with hexosaminidase removed terminal GlcNAc residues to form peaks 5,6 and 7 (panel C). β-galactosidase treatment of peaks 5 and 6 resulted in the formation of isomers 8 and 9 (panel D and E). The proposed structure of each peak is shown in FIGS. 6A–6L.

Partial removal of galactose was accomplished by monitoring the β-galactosidase reaction by reverse phase HPLC, using an RP-HPLC C-18 column and eluting with 12% acetonitrile in 0.1% TFA at 1 ml/min. Fluorescence was detected at an excitation of 275 nm and an emission of 305 nm. Oligosaccharide 1 resolved as a single peak (FIG. 7A) that was converted into 4 peaks at an intermediate time point in the β-galactosidase reaction (FIG. 7B). The numbers assigned to these peaks tentatively corresponded to the structures shown in FIGS. 6A–6L. Hexosaminidase digestion was then used to convert oligosaccharide 2 into 5, oligosaccharide 3 into 6, and oligosaccharide 4 into 7 (FIG. 7C). As expected, oligosaccharide 1 resisted digestion by β-hexosaminidase confirming that it was the biantennary structure presented in FIGS. 6A–6L. Oligosaccharides 5 and 6 were isolated from the mixture and then treated again with β-galactosidase to prepare structures 8 and 9 (FIGS. 7D and 7E).

ES-MS revealed that oligosaccharides 8 and 9 possessed identical masses of 1375 m/z, consistent with the M+1 of the structures proposed in FIGS. 6A–6L. Proton NMR analysis of 8 and 9 also revealed anomeric and N-acetyl resonances associated with the three GlcNAc residues, as well as the anomeric proton for Man 4 and 4'. However, the chemical shift of each resonance was nearly identical for both isomers resulting in an ambiguous identification of each isomer.

Isomers 8 and 9 (1 nmol) were treated for 24 hours at 37° with 20 mU of an α-mannosidase (EC 3.2.1.24 from New England Biolabs) that cleaves α1,2 and α1,3-mannose linkages. Reactions were done in 50 mM sodium citrate buffer, pH 6.0, containing 5 mM $CaCl_2$ and 1 μg bovine serum albumin. The reactions were monitored by RP-HPLC with fluorescence detection as described above, which demonstrated a shift in the retention time for oligosaccharide 8 but not 9. This result established that oligosaccharide 8 possessed a terminal α1,3-linked mannose residue, whereas the terminal α1,6-linked mannose residue on oligosaccharide 9 was not removed by this enzyme. This data leads to the assignments shown in FIGS. 6A–6L.

EXAMPLE 10

Properties of the Purified Xylosyltransferase

The incorporation of xylose from UDP-[$^3$H]xylose into $GlcNAc_2Man_3(GlcNAc)_2$-tyrosinamide by the purified enzyme was linear with time of incubation and with the amount of protein added to the incubation mixtures (data not shown). The pH optimum for enzyme activity was determined using Hepes buffer at a variety of different pH values. The pH profile showed a fairly symmetrical and sharp peak with optimum activity at pH 7.0 and considerably diminished activity above pH 7.5 and below pH 6.5 (data not shown). In terms of enzyme stability, it was also found that the enzymatic activity is most stable when maintained at pH values around 7.0. Surprisingly, the purified xylosyltransferase did not show a requirement for divalent cation. Thus, only a slight stimulation in the activity was observed when 1 mM $MnCl_2$ or $MgCl_2$ were added to the enzyme, or when the enzyme was dialyzed in the presence of EDTA and activity was then measured in the presence of 1 mM $MgCl_2$ (11% stimulation), or 1 mM $CaCl_2$ (15% stimulation). There also was no stimulation in activity by the addition of various other divalent cations such as $Ca^{++}$, $Co^{++}$ or $Fe^{++}$. However, $Pb^{++}$, $Hg^{++}$ and $Fe^{+++}$ were strongly inhibitory when added at concentrations of 1 mM. Most glycosyltransferases do require the presence of a divalent cation, but such a requirement does not appear to apply to the xylosyltransferase. This enzyme may have a bound metal ion that is not removed by dialysis against EDTA.

EXAMPLE 11

Substrate Specificity and Kinetic Constants of the Transferase

The specificity for acceptor substrate was determined using a variety of oligosaccharide substrates that varied in the degree of processing, or in terminal glycosylation. The structures of these acceptors are shown in FIGS. 6A–6L, and their ability to serve as acceptors is indicated in Table 3. Xylosyltransferase activity was measured with both the solubilized enzyme preparation, and with the most purified enzyme. The data demonstrate that the best acceptors are those oligosaccharides having two GlcNAc residues attached to the core mannose oligosaccharide, i.e., structures 4 and 10 of FIGS. 6A–6L. Thus, the presence of the fucose on the innermost GlcNAc appears to have little effect on the addition of xylose.

TABLE 3

Specificity of Plant β1,2-Xylosyltransferase for Oligosaccharide Acceptor

| Oligosaccharide Acceptor | Activity* (cpm xylose transferred) with | |
|---|---|---|
| | Particulate Enzyme | Purified Enzyme |
| No Acceptor | 35 | 98 |
| #1 (see FIG. 4) | 26 | 59 |
| #10 (see FIG. 4) | 3212 | 2387 |
| #4 (see FIG. 4) | 3578 | 3648 |
| GlcNAc-Man$_3$-5'-isomer (#8) | — | 69 |
| GlcNAc-Man$_3$-5-isomer (#9) | — | 1194 |
| #11 (see FIG. 4) | 68 | 56 |
| #7 (see FIG. 4) | 57 | 371 |
| Man$_9$(GlcNAc)$_2$ | 48 | 262 |
| Transferrin | — | 106 |
| Asialo-agalacto-transferrin Peptide | 3215 | 2449 |

*Incorporation of radioactivity form UDP-[$^3$H] xylose into acceptor oligosaccharide was measured by gel filtration on Biogel P-4.

The addition of galactose, however, to the non-reducing terminal GlcNAc residues strongly inhibits activity and oligosaccharides 1, 2 and 3 are ineffective as acceptors of xylose. In addition, core structures 7 and 11 are not active as acceptors of xylose. Interestingly, oligosaccharide 8 is only about 50% as effective as a xylose acceptor as compared to 4, whereas oligosaccharide 9 is completely inactive as an acceptor. These data suggest that xylose is added to the oligosaccharide after the GlcNAc transferase I and GlcNAc transferase II steps (i.e., preferably to oligosaccharide 4). One question with regard to these studies is whether the protein structure is also necessary for, or an effector of, xylosylation. That is, does the enzyme also recognize part of the protein structure so that only storage proteins having a biantennary complex oligosaccharide are substrates for the xylosyltransferase. With sufficient amounts of enzyme available, various plant proteins can be isolated with appropriate oligosaccharide structures in order to compare xylosylation of these intact proteins with xylosylation of denatured proteins, or of glycopeptides or oligosaccharides.

The substrate specificity of the xylosyltransferase for the nucleoside diphosphate sugar donor was also examined, using a variety of radiolabeled sugar nucleotides, as presented in Table 4. Each of these substrates was adjusted to have the same specific activity, and they were compared to each other at that activity. The purified enzyme was very specific for UDP-xylose, and no activity was detected with other uridine diphosphate sugars such as UDP-glucose. Furthermore, addition of unlabeled UDP-glucose, even at 5 mM concentration, did not inhibit the incorporation of xylose into oligosaccharide, indicating that UDP-glucose was not recognized by this enzyme. With the solubilized enzyme preparation, both UDP-xylose and GDP-fucose were active as sugar donors for transfer to oligosaccharide, and some activity was also seen with UDP-GlcNAc. However, neither of these latter two activities were present in the purified xylosyltransferase.

TABLE 4

Specificity of Nucleoside Diphosphate Sugar Donor for Xylosyltransferase

| Sugar Nucleotide Donor | Particulate Enzyme | Purified Enzyme |
|---|---|---|
| | (cpm incorporated into oligosaccharide) | |
| GDP-mannose | 75 | 59 |
| GDP-fucose | 1033 | 142 |
| UDP-xylose | 1479 | 2597 |
| UDP-glucose | 109 | 82 |
| UDP-galactose | 71 | 93 |
| UDP-GalNAc | 72 | 63 |
| UDP-GlcNAc | 246 | 128 |

Enzyme (particulate fraction or purified xylosyltransferase (about 20 ng protein) from UDP-hexanolamine-Sepharose) was incubated with radioactive sugar nucleotide (20,000 cpm; 200 µM) and asialo-agalactotransferrin glycopeptide for 1 hour at 37°. The reaction mixture was then separated on a Biogel P-4 column and radioactivity in oligasaccharide was determined.

Figure 8:
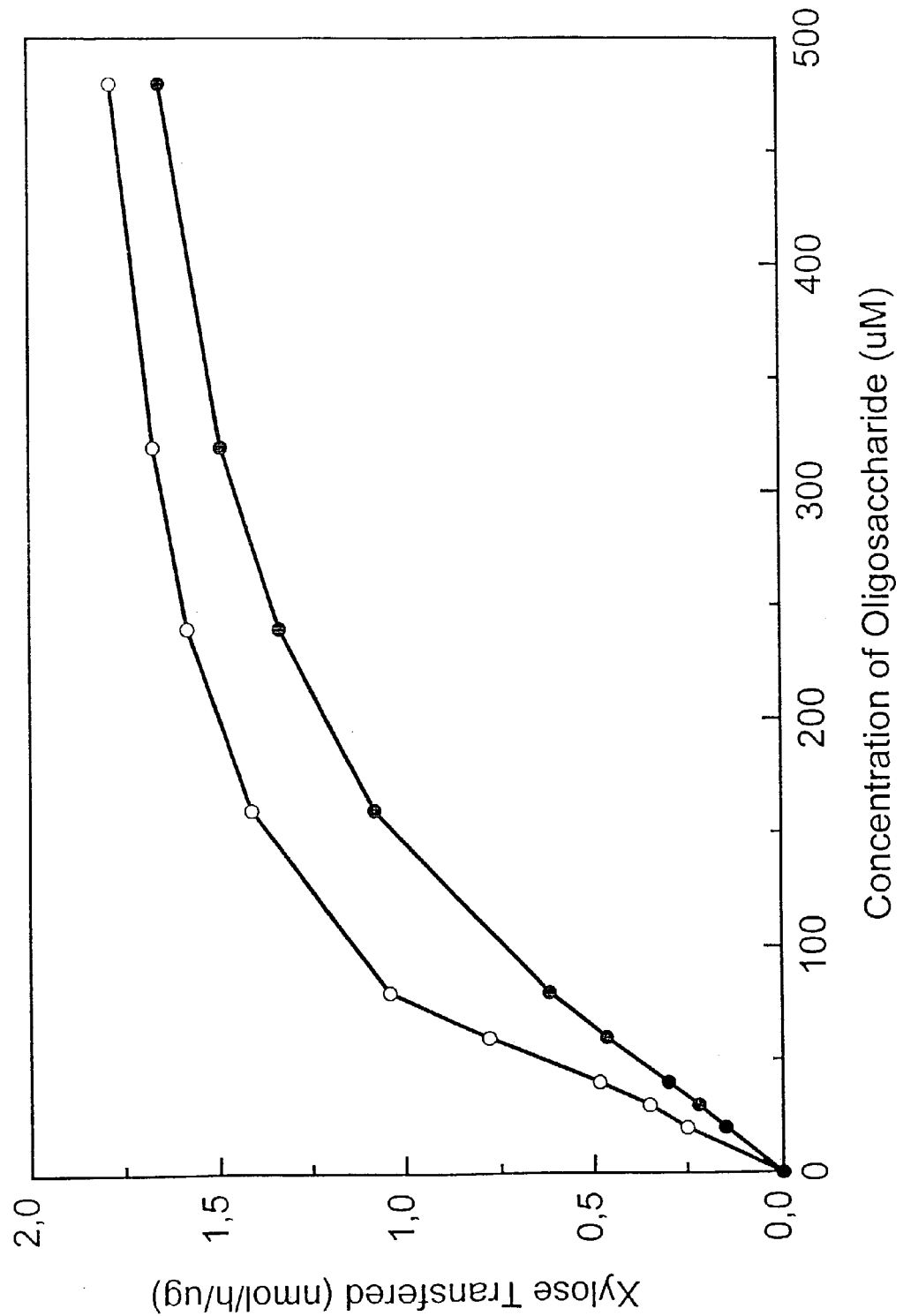
FIG. 8 shows the effect of oligosaccharide substrate concentration on the incorporation of xylose from UDP-xylose into xylosylated oligosaccharide. The effect of increasing concentrations of oligosaccharide 4, i.e., $GlcNAc_2Man3(GlcNAc)_2$-T (o—o) on xylose incorporation is compared to that of oligosaccharide 10, i.e., $GlcNAc_2Man_3GlcNAc(Fuc)GlcNAc$-T (filled circles) to determine which is the best acceptor.
Figure 9:
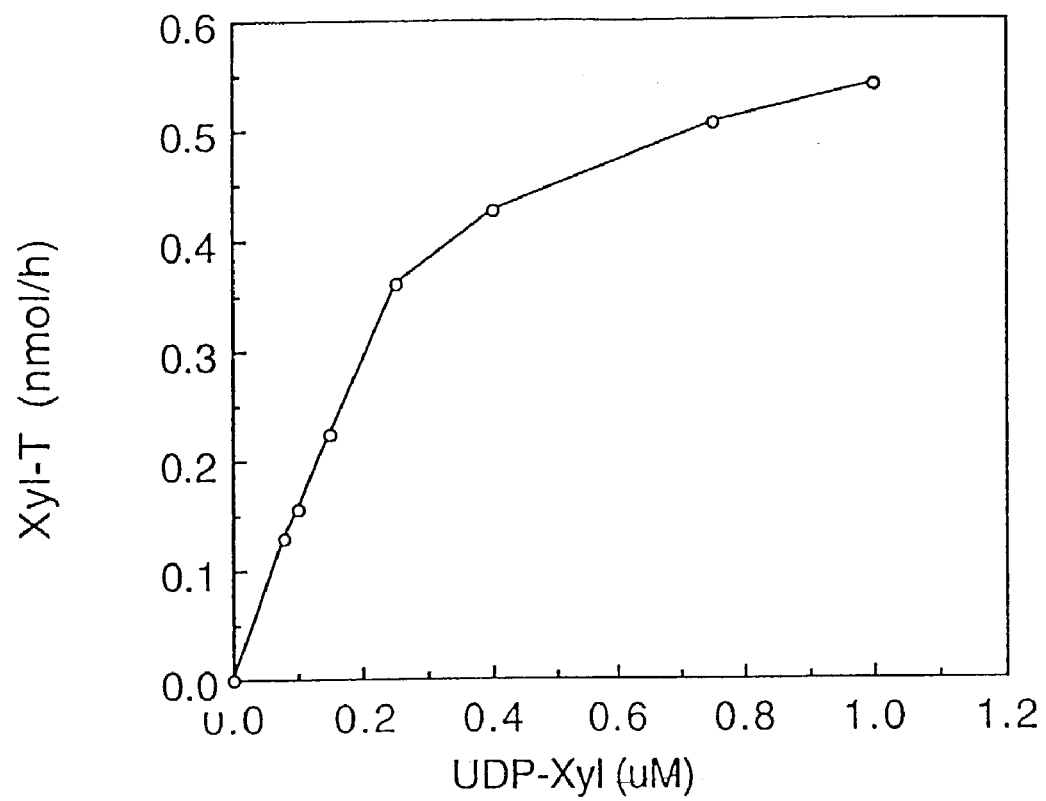
FIG. 9 shows the effect of UDP-xylose concentration on the incorporation of xylose into xylosylated oligosaccharides. Increasing concentrations of UDP-[$^3$H]xylose were added to incubations that contained 5 nmoles of oligosaccharide 4 as well as all of the other reaction components. At the end of the incubation, the amount of xylose transferred to oligosaccharide 4 was measured as described in the experimental methods section.

The effect of oligosaccharide acceptor concentration on the transfer of xylose to the β-linked mannose is shown in FIG. 8. In this experiment, oligosaccharide 4 and oligosaccharide 10 were used as the acceptors, since they were the most active oligosaccharides. The data demonstrate that the reaction rate with oligosaccharide 4 was proportional to the amount of acceptor added, up to concentrations of about 200 µM, and the $K_m$ for acceptor oligosaccharide was determined to be about 75 µM. The other active acceptor, oligosaccharide 10, was also examined at various concentrations, and the $K_m$ for this substrate was calculated to be about 150 µM. The donor substrate in the reaction, i.e., UDP-xylose, was also tested at various concentrations (FIG. 9). In this case also, the reaction rate was proportional to the concentration of UDP-xylose up to about 0.4 µM, and the $K_m$ for UDP-xylose was estimated to be about 0.1 µM.

Based on the substrate specificity for oligosaccharide acceptor, it would appear that xylose is added after the action of GlcNAc transferase I and mannosidase II but before the addition of galactose residues to the terminal GlcNAc units. Most of these types of N-linked oligosaccharides also contain an β1,6-linked L-fucose on the innermost GlcNAc unit. In order to determine whether addition of xylose affects fucose transfer to the oligosaccharide, or vice versa, assays were prepared that contained oligosaccharide 4 as acceptor, radiolabeled nucleoside diphosphate sugar (i.e., either UDP-[$^3$H]xylose or GDP-[$^3$H]fucose) and either unlabeled UDP-xylose or unlabeled GDP-fucose. Thus, when the incubation contained radioactive UDP-xylose, various amounts of unlabeled GDP-fucose were added to determine whether addition of fucose would stimulate or inhibit xylose transfer. Likewise, when labeled GDP-fucose was used, the incubations contained unlabeled UDP-xylose. These incubations were done with the soybean particulate enzyme, so that both fucosyltransferase and xylosyltransferase were present. It can be seen from the data in Table 4 that the addition of UDP-xylose did not affect the incorporation of fucose into the oligosaccharide, suggesting that fucosylation is not dependent on, or inhibited by, prior xylosylation. On the other hand, at high concentrations of GDP-fucose, there appears to be some inhibition of xylose incorporation, suggesting that xylose must be added before the addition of fucose.

EXAMPLE 12

Characterization of the Product Formed by the Xylosyltransferase

The product of the reaction of oligosaccharide 4 and UDP[$^3$H]xylose was isolated by gel filtration on a column of Biogel P-4, and the radioactive oligosaccharide peak was further purified by paper chromatography on acid washed Whatman 3MM paper in ethanol: 1 M ammonium acetate, pH 7.5 (7:3 v/v). The radioactive band was eluted from the paper with water and was subjected to NMR spectroscopy as well as to various glycosidase digestions in order to identify the product. The NMR analysis is entirely consistent with structure 12, having a β1,2-linked xylose on the β-linked mannose. The product was also susceptible to digestion by β-hexosaminidase which gave a radioactive product (P1) that migrated more slowly on a long calibrated column (200 cm) of Biogel P-4 than the original oligosaccharide by an amount indicative of the loss of 2 GlcNAc residues. The hexosaminidase-treated oligosaccharide was also susceptible to digestion by jack bean β-mannosidase, and this digestion gave a second product (P2) that moved more slowly on Biogel P-4 suggesting the loss of 2 hexose residues. The NMR and the glycosidase digestion data confirm that the product is indeed the structure shown in FIG. 6L.

EXAMPLE 13

Sequence

The product of the reaction of UDP-xylose and a good acceptor, i.e., GlcNAc$_2$Man$_3$(GlcNAc)$_2$T was characterized by NMR as GlcNAcβ1,2Manα1,6Manα1,6[GlcNAcβ1,3](Xylβ1,2)Manβ1,4[Glc NAc)$_2$-T. The purified XT was separated on SDS gels into the 56 and 59 kDa bands, and each protein was obtained in sufficient amounts (about 20 ug o f each) to send to Harvard Microchemistry Labs for digestion, isolation of peptides and sequencing of several peptides. These peptide sequences are shown below.

Peptide 1: 56 kDa band

Amino Acids: L S N E Q E V F D S L K (SEQ ID No. 1)
Peptide 2: 56 kDa band

Amino Acids: V L V D Q E F L D E Y V P R (SEQ ID No. 2)
Peptide 3: 56 kDa band

Amino Acids: S Q V Q A I H D A S V I I G A H G A G L T H I V S A L (SEQ ID No. 3)
Peptide 1: 59 kDa band Amino Acids: E L L V D Q E F L D E Y V P R (SEQ ID No. 4)
Peptide 2: 59 kDa band Amino Acids: G L E Y H A I N L G (SEQ ID No. 5)

The amino acid sequence of peptide 2 of the 56 kDa band and the peptide 1 of the 59 kDa band are almost identical and the peptide maps of the two proteins are quite similar suggesting considerable similarity. However, there are enough differences t o indicate that the removal of a 3 kDa from the N- or C-terminus may not explain these differences.

The plant enzyme that adds β-1,2-linked xylose to the β-linked mannose on the N-linked oligosaccharides of storage glycoproteins was purified. While some of the properties of a β1,2-xylosyltransferase have been reported with enzyme systems from the snail, Lymnaea stagnalis (17), as well as the plant enzymes from Phaseolus vulgaris (15) and from Acer pseudoplatanus (16), this is the first report of the purification of this enzyme. The β1,2-xylosyltransferase was purified from the microsomal fraction of soybean cells approximately 51,000-fold to apparent homogeneity. This purified fraction gave two major protein bands of 56 and 59 kDa on SDS gels, and both of these protein bands were specifically labeled by the photoaffinity label, $N_3$-UDP[$^{32}$P]-xylose. In addition, the labeling was inhibited in a concentration-dependent manner by adding unlabeled UDP-xylose, but other UDP-sugars like UDP-glucose did not inhibit. Thus, both proteins recognize UDP-xylose and are likely to be catalytic units of the xylosyltransferase.

Sufficient amounts of these proteins were purified to obtain amino acid sequences of several peptides. Importantly, the peptide maps of the 2 proteins, prepared by Endo lys C digestion, were similar but contained enough differences to indicate that the 56 kDa protein could not have come directly from the 59 kDa protein by removal of a 3 kDa peptide. This suggests that these two proteins arose by gene splicing. The amino acid sequences obtained from the two xylosyltranssferase proteins did not show strong identity or homology to sequences from other known proteins in a BLAST search.

Based on these results and the oligosaccharide acceptor specificity, it seems likely that the β1,2-xylosyltransferase is a medial or trans-Golgi enzyme that recognizes a GlcNAc on the α1,3-mannose of the tri-mannose structure, but also requires a GlcNAc on the α1,6-mannose as well. One may prepare a polyclonal antibody to be utilized in localization of the protein in suspension cultured soybean cells. This antibody will also be useful to determine the distribution and level of this enzyme in various other plants as well as its levels at various stages of growth. Such data can be compared to levels of mRNA for this protein once the enzyme has been cloned and cDNA is available.

FIG. 10 shows the nucleotide sequence of the cDNA clone of xylosyltransferase (SEQ ID No. 6). The oligosaccharide specificity reported here is somewhat different than the acceptor specificities reported for the other xylosyltransferases. For example, the enzyme from sycamore cells showed better activity with the trimannose structure with a GlcNAc on the 3-branched mannose (FIG. 6I) than it did with the di-GlcNAc oligosaccharide (FIG. 6D). In addition, reasonable activity was also observed with the GlcNAc-$Man_5$-oligosaccharide (16). On the other hand, the snail enzyme was more like the soybean enzyme and showed best activity with the di-GlcNAc structure but reasonable activity with structure 9 (17).

One of the questions that can be addressed with the purified enzyme is whether the protein structure of the acceptor glycoprotein, that is the storage glycoprotein, is a factor in the addition of xylose to these proteins. That is, in addition to recognizing a specific oligosaccharide structure for the addition of xylose, does the β1,2-xylosyltransferase also recognize specific proteins that are destined to be localized in storage bodies. There is precedence for glycosyltransferases recognizing both the oligosaccharide acceptor and the protein to be glycosylated. Thus, the signals for targeting lysosomal enzymes to the lysosomes are the presence of phosphate residues on several mannose residues of the high-mannose oligosaccharides. These phosphates are added by the transfer of GlcNAc-1-P from UDP-GlcNAc via a GlcNAc-1-P phosphotransferase. This enzyme recognizes not only high-mannose oligosaccharides but specifically oriented lysine residues on those proteins destined to become lysosomal enzymes. A similar situation exists with respect to glycosylation of some of the glycoprotein hormones where the GalNAc transferase recognizes both the carbohydrate acceptor and some specific region(s) of the glycoprotein hormone.

A person having ordinary skill in this art may also prepare oligonucleotides from the peptide sequences and use these to clone the gene for this enzyme from a soybean library. These studies can lead to the production of antisense oligonucleotides to inhibit the synthesis of the β1,2-xylosyltransferase. Such experiments could be of considerable importance to produce a plant that cannot add xylose to its N-linked oligosaccharides. Such glycoproteins might be considerably less allergenic. It will also be of interest to transfect this gene into animal cells to determine the effect of xylosylation of animal glycoproteins on their targeting and function. Finally, the gene can be utilized for site directed mutagenesis studies to determine essential features of the enzyme.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An isolated antibody directed against an isolated and purified soybean enzyme, β1,2-xylosyltransferase, said enzyme is encoded by a cDNA comprising the sequence of SEQ ID NO. 6.

2. The antibody of claim 1, wherein digestion of said enzyme by Endo lys C produces a set of proteolytic fragments having a set of sequences comprising SEQ ID NOs. 1–3.

3. The antibody of claim 1, wherein said enzyme is obtained from the microsomal fraction of soybean cells.

4. The antibody of claim 1, wherein said enzyme has a molecular weight of 56 kDa as determined on SDS gels.

* * * * *

SEQUENCE LISTING

<160> NUMBER OF SEQ ID NOS: 7

<210> SEQ ID NO 1
<211> LENGTH: 12
<212> TYPE: PRT
<213> ORGANISM: soybean
<220> FEATURE:
<223> OTHER INFORMATION: Amino acid sequence of a peptide released
      by Endo lys C digestion of purified
      xylosyltransferase.

<400> SEQUENCE: 1

Leu Ser Arg Glu Gln Glu Val Phe Asp Ser Leu Lys
                5                   10

<210> SEQ ID NO 2
<211> LENGTH: 14
<212> TYPE: PRT
<213> ORGANISM: soybean
<220> FEATURE:
<223> OTHER INFORMATION: Amino acid sequence of a peptide released
      by Endo lys C digestion of purified
      xylosyltransferase.

<400> SEQUENCE: 2

Val Leu Val Asp Gln Glu Phe Leu Asp Glu Tyr Val Pro Arg
                5                   10

<210> SEQ ID NO 3
<211> LENGTH: 27
<212> TYPE: PRT
<213> ORGANISM: soybean
<220> FEATURE:
<223> OTHER INFORMATION: Amino acid sequence of a peptide released
      by Endo lys C digestion of purified
      xylosyltransferase.

<400> SEQUENCE: 3

Ser Gln Val Gln Ala Ile His Asp Ala Ser Val Ile Ile Gly Ala
                5                   10                  15

His Gly Ala Gly Leu Thr His Ile Val Ser Ala Leu
                20                  25

<210> SEQ ID NO 4
<211> LENGTH: 15
<212> TYPE: PRT
<213> ORGANISM: soybean
<220> FEATURE:
<223> OTHER INFORMATION: Amino acid sequence of a peptide released
      by Endo lys C digestion of purified
      xylosyltransferase.

<400> SEQUENCE: 4

Glu Leu Leu Val Asp Gln Glu Phe Leu Asp Glu Tyr Val Pro Arg
                5                   10                  15

<210> SEQ ID NO 5
<211> LENGTH: 10
<212> TYPE: PRT
<213> ORGANISM: soybean
<220> FEATURE:
<223> OTHER INFORMATION: Amino acid sequence of a peptide released
      by Endo lys C digestion of purified
      xylosyltransferase.

-continued

```
<400> SEQUENCE: 5

Gly Leu Glu Tyr His Ala Ile Asn Leu Gly
                5                   10

<210> SEQ ID NO 6
<211> LENGTH: 800
<212> TYPE: DNA
<213> ORGANISM: artificial sequence
<220> FEATURE:
<223> OTHER INFORMATION: Nucleotide sequence of cDNA clones of
      purified xylosyltransferase.

<400> SEQUENCE: 6
aggttctggt tgaccaagag ttttggatga gtatgtgcca aggggaggga ttgatagaca     60
caccatgcgg gatttgatcg ccaagattcg gatcgtgaga gggaaggatt ttcaatgtga    120
tgagtggatt gaggaaccaa cacttctggt gacacgtttt gagtatgcta atctttttca    180
cactgttaca gactggtaca gtgcttatgt ttcttctaga gtcaccgctc tgcctaatcg    240
acctcatgtg atctttgttg atggccactg taaggctcct cttgaagaga catggaaagc    300
cttattctca agcgtcggat atgctaagag cttcagtggt tcagtttgtt ttcatcatgc    360
tattctctca cccttgggat atgagacggc aatgtttaga gggctttcag aacatataga    420
ttgttatgga gctcctgcac aagaactatt gcaaaacctt aatgaccaca aaaccgcgcg    480
cctttctgag tttggagaaa tggtcagagc agcttttggg ctacctttaa atgtaaacca    540
tgatggaaaa ccactcgctg acataatgt cctctttgtt cgtcgcgaag attatttagc     600
tcatccacgt cacagtggga aacttgaatc acgactaagt aacgagcaag aagtcttcaa    660
ctcgttgaag agctgggcat ccaattataa agggtgtaaa attaaccttg tcaacggatt    720
gtttgctcac atgtctatga aggatcaggt tcaagccatt catgatgcat cggtcatcat    780
tggcgcccat ggtgccggtc                                                800

<210> SEQ ID NO 7
<211> LENGTH: 778
<212> TYPE: DNA
<213> ORGANISM: artificial sequence
<220> FEATURE:
<223> OTHER INFORMATION: Nucleotide sequence of PCR product of
      purified xylosyltransferase.

<400> SEQUENCE: 7
gagtttctgg atgagtatgt gccaagggga gggattgata cacaccat gcgggatttg      60 atcgccaaga ttcggatcgt gagagggaag gattttcaat gtgatgagtg gattgaggaa    120
ccaacacttc tggtgacacg ctctgagtat gctaatcttt ttcacactgt tacagactgg    180
tacagtgctt atgtttcttc tagagtcacc gctctgccta atcgacctca tgtgatcttt    240
gttgatggcc actgtaaggc tcctcttgaa gagacatgga aagccttatt ctcaagcgtc    300
agatatgcta agagcttcag tggttcagtt tgttttcatc atgctattct ctcacccttg    360
ggatatgaga cggcaatgtt tagagggctt tcagaacata tagattgtta tggagctcct    420
gcacaagaac tattgcaaaa ccttaatgac cacaaaaccg cgcgcctttc tgagtttgga    480
gaaatggtca gagcagcttt tgggctacct ttaaatgtaa accatgatgg aaaaccactc    540 gctgacata atgtcctctt tgttcgtcgc gaagattatt tagctcatcc acgtcacagt     600
gggaaacttg aatcacgact aagtaacgag caagaagtct tcaactcgtt gaagagctgg    660
```

```
gcatccaatt ataaagggtg taaaattaac cttgtcaacg gattgtttgc tcacatgtct    720
atgaaggatc aggttcaagc cattcatgat gcatcggtca taatcggcgc ccatggag     778
```